(12) United States Patent
Saito et al.

(10) Patent No.: US 8,642,796 B2
(45) Date of Patent: Feb. 4, 2014

(54) ORGANORUTHENIUM COMPOUND FOR CHEMICAL DEPOSITION AND CHEMICAL DEPOSITION PROCESS USING THE ORGANORUTHENIUM COMPOUND

(75) Inventors: Masayuki Saito, Tsukuba (JP);
Kazuharu Suzuki, Tsukuba (JP);
Shunichi Nabeya, Tsukuba (JP)

(73) Assignee: Tanaka Kikinzoku Kogyo K. K., Tokyo (JP)

( * ) Notice: Subject to any disclaimer, the term of this patent is extended or adjusted under 35 U.S.C. 154(b) by 322 days.

(21) Appl. No.: 13/161,012

(22) Filed: Jun. 15, 2011

(65) Prior Publication Data
US 2011/0318488 A1 Dec. 29, 2011

(30) Foreign Application Priority Data
Jun. 24, 2010 (JP) ................................ P2010-143391

(51) Int. Cl.
*C07F 15/00* (2006.01)
*C23C 16/00* (2006.01)

(52) U.S. Cl.
USPC ............................. 556/41; 556/136; 427/252

(58) Field of Classification Search
USPC ..................................... 556/41, 136; 427/252
See application file for complete search history.

(56) References Cited

U.S. PATENT DOCUMENTS

| 6,743,934 B2 | 6/2004 | Saito et al. | 556/40 |
| 2003/0203102 A1 | 10/2003 | Saito et al. | 427/132 |

FOREIGN PATENT DOCUMENTS

JP 2003-306472 10/2003

OTHER PUBLICATIONS

Cheng W-Y, et al. "Initial Growth of Chemical-Vapor-Deposited Ru From bis(hexafluoroacetylacetonate) dicarbonyl ruthenium." Thin Solid Films, vol. 483, No. 1-2, Jul. 1, 2005, pp. 31-37.
Lai Y-H, et al. "Deposition of Ru and RuO2 thin films employing dicarbonyl bis-diketonate Ruthenium complexes as CVD source reagents," Journal of Materials Chemistry, vol. 13, No. 8, Jun. 9, 2003, pp. 1999-2006.
Chen R-S et al. "Preparation and characterization of RUO2 thin films from RU(CO)2(tmhd)2 by Metalorganic chemical vapor deposition." Thin Solid Films, vol. 413, No. 1-2, Jun. 24, 2002, pp. 85-91.
Lee F-J et al. "Organometallic Ruthenium Source Reagents for CVD." Chemical Vapor Deposition, vol. 7, No. 3, May 2001, pp. 99-101.

*Primary Examiner* — Porfirio Nazario Gonzalez
(74) *Attorney, Agent, or Firm* — Richard S. Roberts

(57) ABSTRACT

An object of the present invention is to provide an organoruthenium compound which has good film formation characteristics as an organoruthenium compound for chemical deposition, has a high vapor pressure, and can easily form a film even when hydrogen is used as a reactant gas. The present invention relates to an organoruthenium compound, dicarbonyl-bis(5-methyl-2,4-hexanediketonato)ruthenium (II) which can have isomers 1 to 3, wherein the content of the isomer 2 is 30% by mass or more, the content of the isomer 3 is 30% by mass or less, and the balance is the isomer 1.

4 Claims, 5 Drawing Sheets

¹H-NMR (400MHz, CDCl₃) δ ; 5.41 - 5.38 (s, 2H, CH), 2.55 - 2.40 (sept., J = 8.9 Hz, 2H, CH), 2.07 - 2.03 (s, 6H, CH3), 1.09-1.00 (d, J = 8.9 Hz, 12H, CH3)

ORGANORUTHENIUM COMPOUND FOR CHEMICAL DEPOSITION AND CHEMICAL DEPOSITION PROCESS USING THE ORGANORUTHENIUM COMPOUND

TECHNICAL FIELD

The present invention relates to an organoruthenium compound used as a raw material for producing a ruthenium thin film or a ruthenium compound thin film by a CVD process or an ALD process. Particularly, the present invention relates to an organoruthenium compound which is liquid at ordinary temperatures and has a high vapor pressure.

BACKGROUND ART

Ruthenium or ruthenium compounds have been used as a material for thin film electrodes of semiconductor devices such as DRAM and FERAM. A chemical deposition process such as a CVD process (chemical vapor deposition process) or an ALD process (atomic layer deposition process) is applied to the production of these thin films. Many organoruthenium compounds have been known as raw material compounds used in such a chemical deposition process.

As an organoruthenium compound for chemical deposition as described above, the present inventors have disclosed a compound in which two β-diketones and one diene (norbornadiene, cyclooctadiene, or the like) are coordinated, such as a compound represented by formula 1 (Patent Literature 1). When a thin film is formed with the compound represented by formula 1, a film which is uniform and has high denseness can be easily obtained.

[Formula 1]

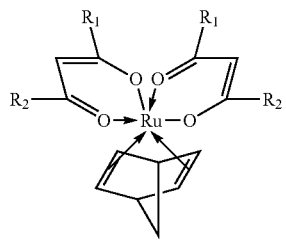

(R1 and R2 each represent an alkyl group.)

Generally, characteristics required for an organoruthenium compound for chemical deposition include a high vapor pressure for efficiently forming a thin film. Further, when handlability is taken into consideration, the organoruthenium compound is preferably in a liquid state at ordinary temperatures. From such a point of view, the present inventors have disclosed, in Patent Literature 1, a compound with a low molecular weight in which the substituents ($R_1$, $R_2$) of β-diketones in the compound represented by formula 1 have carbon atoms in a predetermined range. Such a compound has a relatively high vapor pressure, easily maintains a liquid state at ordinary temperatures, and satisfies the above characteristics.

CITATION LIST

Patent Literature

[Patent Literature 1] Japanese Patent Laid-Open No. 2003-306472

SUMMARY OF INVENTION

Problems to be Solved by the Invention

However, when chemical deposition is performed using hydrogen as a reactant gas, it is hard to form a ruthenium thin film with the compound represented by formula 1, and it is necessary to set the reaction temperature at a relatively high temperature in order to form a film. When a film is deposited on a substrate made of an easily oxidized material such as titanium nitride, it is required that chemical deposition using hydrogen can be easily performed so that degradation of the substrate may be prevented.

Thus, an object of the present invention is to provide an organoruthenium compound which has good deposition characteristics as an organoruthenium compound for chemical deposition, has a high vapor pressure, and can easily form a film even when hydrogen is used as a reactant gas.

Means for Solving the Problems

The present inventors paid their attention to a compound represented by formula 2 in order to solve the aforementioned problems. The compound represented by formula 2 can easily form a film even when hydrogen is used as a reactant gas.

[Formula 2]

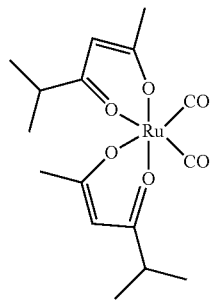

However, when the compound represented by formula 2 was actually synthesized under various synthesis conditions, the compound was not in a liquid state at ordinary temperatures in some cases. Therefore, the present inventors have studied the conditions for the case where the compound represented by formula 2 is in a liquid state at ordinary temperatures, and when the present inventors paid attention to the point that the compound represented by formula 2 can have three isomers, they have found that the compound tends to be in a liquid state at ordinary temperatures when the content of an isomer in the compound is in a specific range, and have hit upon the present invention.

Hereinafter, the present invention will be described in detail. First, the compound represented by formula 2 can have the following three isomers 1 to 3 in which the configuration of β-diketones which are coordinated to the ruthenium metal is different (refer to formula 3). These three isomers are geometrical isomers in which the configuration of isopropyl groups and methyl groups in the diketonate ligands (β-diketones) is different.

[Formula 3]

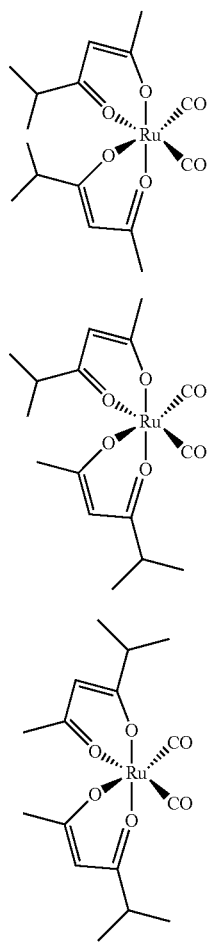

The organoruthenium compound of the present invention relates to an organoruthenium compound in which, in the above three isomers, the content of the isomer 2 is 30% by mass or more, and the content of the isomer 3 is 30% by mass or less, and the balance is the isomer 1. Such an organoruthenium compound easily maintains a liquid state at ordinary temperatures. As for the content of isomers in the compound, it is preferred that the content of the isomer 2 be 40% by mass or more, the content of the isomer 3 be 20% by mass or less, and the balance be the isomer 1. More preferably, the content of the isomer 2 is 40% by mass or more, the content of the isomer 3 is 18% by mass or less, and the balance is the isomer 1. Such a compound will easily form a film having a low specific resistance even when hydrogen is used as a reactant gas in forming a thin film.

As described above, the organoruthenium compound of the present invention has a high vapor pressure and can stably maintain a liquid state at ordinary temperatures. Therefore, when a thin film is formed, a film which is uniform and has high denseness can be easily obtained, and chemical deposition in the case where hydrogen is used as a reactant gas is relatively easily performed. Consequently, it is suitable as a raw material compound for use in the chemical deposition process for forming a ruthenium thin film or a ruthenium compound thin film.

Here, the content of each isomer in the organoruthenium compound can be determined by measuring a $^1$H-NMR spectrum and calculating the area ratio of the peaks derived from the isomers. Thus, the content (mass ratio) of the isomers can be determined from the peak area ratio of the $^1$H-NMR spectrum because each isomer has the same molecular weight and the same number of hydrogen atoms (two) assigned to methine sites.

Specifically, the $^1$H-NMR spectrum is first measured, and the peaks in a chemical shift value ($\delta$) of 5.42 to 5.38 ppm derived from the methine groups (=C—) of β-diketones are observed. In this spectrum, the peak appearing in the vicinity of $\delta$ 5.42 ppm is derived from the isomer 3. Further, the peaks in the vicinity of $\delta$ 5.40 ppm and $\delta$ 5.38 ppm are derived from the isomer 2, and the peak in the vicinity of $\delta$ 5.39 ppm is derived from the isomer 1.

Then, the content of the isomers in the present invention can be determined by calculating the area ratio of the peaks appearing in the $^1$H-NMR spectrum measurement. Specifically, the peak area ratio ($\delta$ 5.39 ppm:$\delta$ 5.40 ppm+5.38 ppm:$\delta$ 5.42 ppm) serves as the content of the isomers (isomer 1:isomer 2:isomer 3). Note that, in the present invention, the $^1$H-NMR spectrum is measured in a deuterated chloroform solvent using tetramethylsilane as a reference material.

In the present invention, it is possible to calculate, in this way, the content ratio of each isomer based on the correspondency with the appearing peaks in the $^1$H-NMR spectrum because the present inventors have succeeded in the isolation of the three isomers which has been difficult. A specific isolation method and the like will be described in detail below, but it was possible to calculate the content ratio of each isomer because it was possible to specify the appearing peak and the like in the $^1$H-NMR spectrum corresponding to each isomer since it became possible to analyze the X-ray crystal structure and measure the $^1$H-NMR spectrum for each isolated isomer.

An organoruthenium compound in which the content of the isomer 2 is 30% by mass or more, the content of the isomer 3 is 30% by mass or less, and the balance is the isomer 1, as described in the present invention, can be produced by a production method in which decane is used as an organic solvent and reaction temperature is maintained at 140 to 160° C. Specifically, dicarbonyl-bis(5-methyl-2,4-hexanediketonato)ruthenium (II) which is the organoruthenium compound according to the present invention is produced by using triruthenium dodecacarbonyl as a starting material and allowing it to react with 5-methyl-2,4-hexanedione according to the reaction as shown in Expression 1. This reaction is preferably performed with reflux in an organic solvent at 140 to 160° C. for 10 to 100 hours. A solvent having a high boiling point is useful as an organic solvent, and in particular decane (dry decane) is preferred. Further, the resulting product is preferably distilled.

[Expression 1]

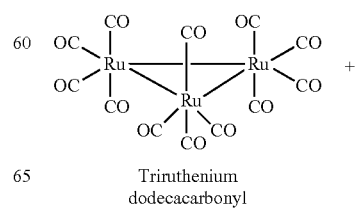

Triruthenium
dodecacarbonyl

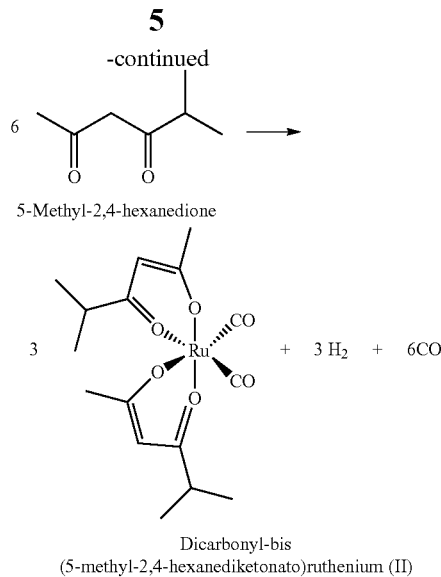

It is also preferred to isolate the isomers 1 to 3 from dicarbonyl-bis(5-methyl-2,4-hexanediketonato)ruthenium (II) obtained by the above production method or other methods and then mix each isomer so that the content of each isomer may be within a suitable range of content, thus obtaining an organoruthenium compound. This is because an organoruthenium compound which easily maintains a liquid state at ordinary temperatures can be produced. In this case, the isomers have been mixed so that the content of each isomer may be within a suitable range of content by adjusting the weight ratio of each isomer. In addition, a method by column chromatography can be used as a purification method for isolating each isomer, wherein silica gel is preferred as a filler.

Here, the above purification method will be described in detail. Conventionally, among the three isomers, the isomer 1 has been relatively easily isolated, but there has been a tendency that the remaining isomers 2 and 3 are hardly separated from each other, and it has been difficult to specify the peak derived from the isomer 2 and the peak derived from the isomer 3 in the $^1$H-NMR spectrum and the like. Therefore, it has been impossible to specify the content of the isomer which is easily in a liquid state only by measuring the $^1$H-NMR spectrum and the like of the resulting compound. Then, the present inventors have conducted intensive studies this time to isolate all of the isomers. As a result, it has been found that all the isomers 1, 2, and 3 can be isolated by improving the separation ability of chromatography by increasing the amount of a filler such as silica gel and adjusting the composition of a developing solvent, in the purification by column chromatography.

Specifically, although the amount of a filler relative to the fluid volume of a compound to be purified (volume ratio) has conventionally been 1:10 to 1:20, the ratio of the filler has been increased to 1:20 to 1:50. In addition, the diameter of a column to be used has been increased. Further, with respect to the developing solvent, for example, when a mixture of hexane and ethyl acetate is used, these solvents have been conventionally used at a volume ratio of hexane to ethyl acetate of 2:1 to 3:1, but the amount of hexane, which has a low polarity, has now been increased to 20:1. Separation ability has been able to be significantly increased by modifying the purification method as described above, and the present inventors have succeeded in the separation of the isomer 2 and the isomer 3 which had conventionally been difficult.

Advantageous Effects of Invention

As described above, the organoruthenium compound according to the present invention has a relatively high vapor pressure and is in a liquid state at ordinary temperatures. In addition, it has good film formation characteristics in forming a thin film by a chemical deposition process.

MODE FOR CARRYING OUT THE INVENTION

First Embodiment

Figure 1:
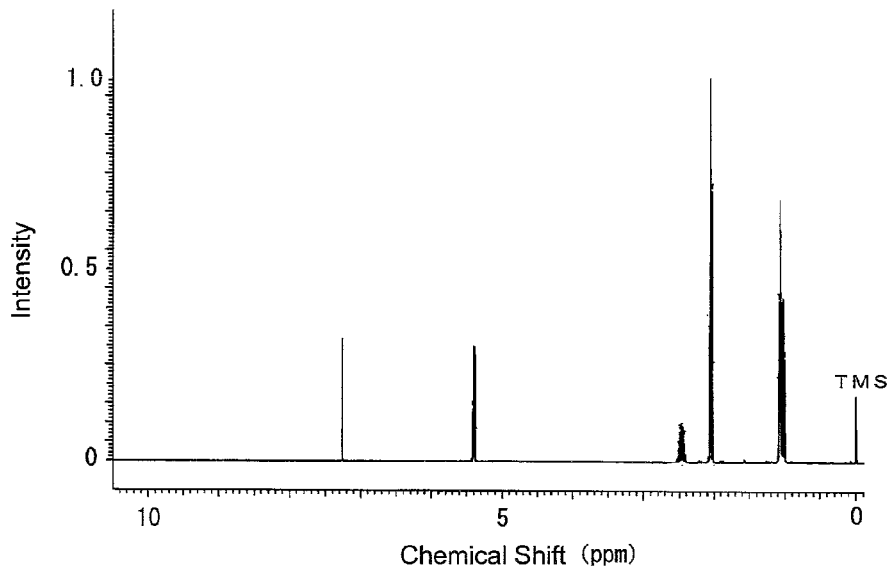
FIG. 1 is a $^1$H-NMR spectrum of the organoruthenium compound of a first embodiment.

First, an organoruthenium compound was produced by an industrial synthetic method, and the produced compound was subjected to $^1$H-NMR measurement to identify the kind of isomers contained. Subsequently, the peaks observed in the $^1$H-NMR measurement were specified from which isomers 1 to 3 they were derived by the isolation of each isomer, X-ray crystal structure analysis, and the like. Further, the isomers isolated were mixed in a specific content and observed whether the compound would be in a liquid state, or the like. Furthermore, the measurement of physical properties and a film formation test were performed to verify whether the compound would be suitable for producing a ruthenium thin film.

Production of the Organoruthenium Compound

Dicarbonyl-bis(5-methyl-2,4-hexanediketonato)ruthenium (II) was produced by the following method. A three necked flask purged with nitrogen gas was charged with 40.8 g of triruthenium dodecacarbonyl as a starting material (63.8 mmol, manufactured by Tanaka Kikinzoku Kogyo K.K.), 2000 ml of dry decane as an organic solvent (manufactured by Sigma-Aldrich Japan K.K.), and 51.6 g of 5-methyl-2,4-hexanedione (402 mmol, manufactured by Tanaka Kikinzoku Kogyo K.K.). These compounds were allowed to react with each other under ordinary pressure at a solution temperature of 145° C. for 36 hours with heating and stirring. Subsequently, the resulting mixture was cooled to room temperature, and an orange colored powder of unreacted triruthenium dodecacarbonyl was filtered to obtain a product. The solvent was removed from the product with an evaporator, and the resulting orange colored liquid was distilled twice under a reduced pressure (155° C., 320 Pa). The resulting compound was a yellow liquid at ordinary temperatures (56.5 g, 137 mmol, yield 72%).

$^1$H-NMR Measurement

The organoruthenium compound produced as described above was measured for the $^1$H-NMR spectrum. The measurement of $^1$H-NMR was performed by dissolving the organoruthenium compound in 99.8% deuterated chloroform solution and using a nuclear magnetic resonance apparatus manufactured by JEOL Ltd. (JNM-ECS400, resonance frequency 400 MHz). The measurement conditions include a sample concentration of 1%, an integration count of 32 times, and a measurement temperature of 25° C. The results of the measured spectrum and an enlarged view of chemical shift values (δ) in the range of 5.35 to 5.45 ppm are shown in FIG. 1 and FIG. 2, respectively.

Figure 2:
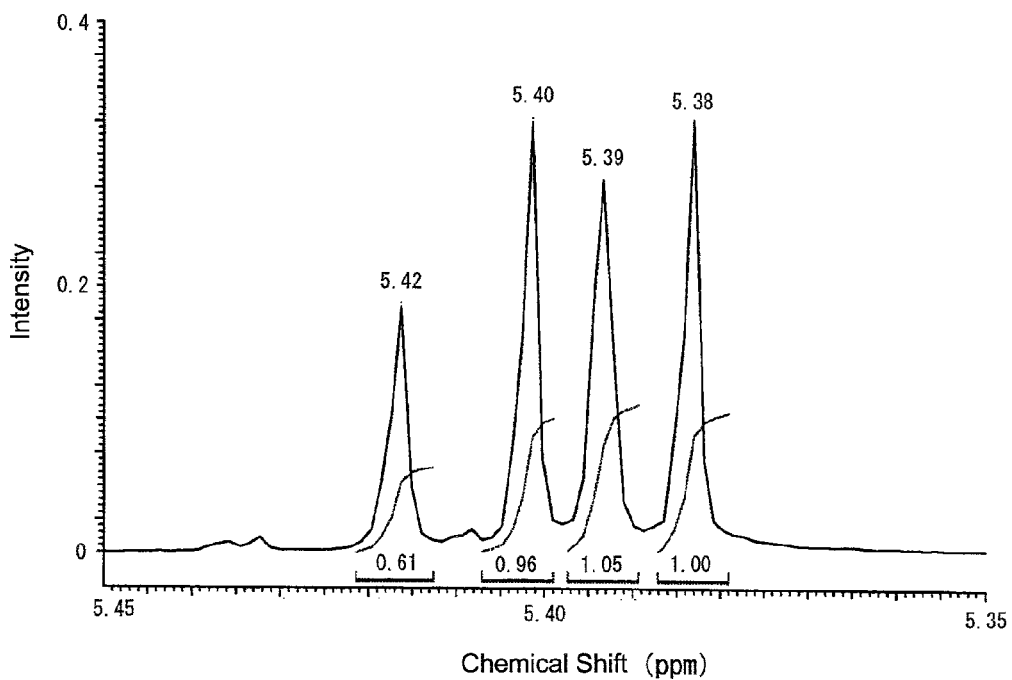
FIG. 2 is an enlarged view of the $^1$H-NMR spectrum of the organoruthenium compound of the first embodiment.

The $^1$H-NMR spectrum shown in FIGS. 1 and 2 has revealed four peaks showing the presence of four non-equivalent protons in the vicinity of δ 5.35 to 5.45 ppm. On the other hand, the isomers 1 to 3, which the organoruthenium compound of the present invention can have, have four kinds of protons non-equivalent to each other as shown by (1) to (4) in formula 4. As described above, it has been found that the isomers 1 to 3 are included in the produced compound because the $^1$H-NMR spectrum has suggested that four non-equivalent protons are included. Note that the peak area calculated for each peak of the $^1$H-NMR spectrum was 0.61, 0.96, 1.05, and 1.00 for the peaks at δ 5.42 ppm, δ 5.40 ppm, δ 5.39 ppm, and δ 5.38 ppm, respectively.

[Formula 4]

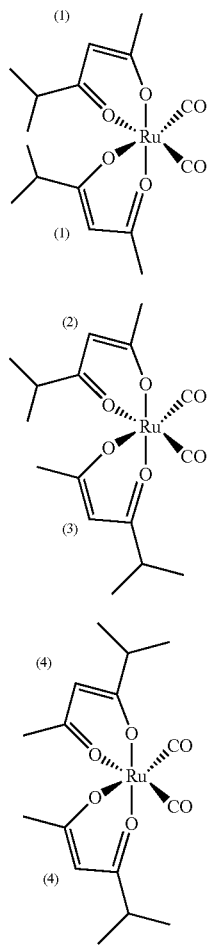

Here, since the compound includes all of the isomers 1 to 3, it was unknown from which isomers 1 to 3 each peak of the $^1$H-NMR spectrum was derived. Therefore, the present inventors assumed, for convenience, the isomer having a peak in the vicinity of a chemical shift value (δ) of 5.42 ppm in the $^1$H-NMR spectrum as "isomer A", the isomer having peaks in the vicinity of δ 5.40 ppm and δ 5.38 ppm as "isomer B", and the isomer having a peak in the vicinity of δ 5.39 ppm as "isomer C". The following is the reason why the two peaks in the vicinity of δ 5.40 ppm and in the vicinity of δ 5.38 ppm among the four peaks were assumed to be derived from the isomer B as described above.

When the present inventors observed the $^1$H-NMR spectrum for a plurality of compounds having different isomer content, the two peaks in the vicinity of δ 5.40 ppm and in the vicinity of δ 5.38 ppm had almost the same shape, such as height and line width of the peaks, and almost the same peak area ratio in the spectra of all the compounds. Therefore, the present inventors have thought that these two peaks are derived from the isomer 2 which has two diketone ligands each having different methine site protons and in which each proton is expected to be observed with the same intensity. This is the reason why they have assumed that these peaks are derived from the isomer B.

Then, the correspondence of the isomers A to C included in the organoruthenium compound obtained by the synthetic method according to the first embodiment to the isomers 1 to 3 specified by the structure of the isomers has been determined based on the following experiments and the like.

Isolation of the Isomers

First, in order to isolate each isomer included in the organoruthenium compound obtained by the above synthetic method, purification by column chromatography was performed. A column pipe having a diameter of 100 mm was filled with 2000 g of silica gel, Wako gel C300 (manufactured by Wako Pure Chemical Industries, Ltd.) to perform column chromatography. The column was charged with 50 g of the organoruthenium compound obtained by the above method, and then the column was developed at a flow rate of 10 ml/min with a mixed solvent of hexane and ethyl acetate (hexane: ethyl acetate=20:1 (volume ratio)) as an eluent.

Then, the eluent eluted from the column pipe was collected, divided into fifty 100-ml fractions (5 L in total). Each collected fraction was subjected to gas chromatograph and $^1$H-NMR spectrum measurement to select a fraction which contains any of the isomers 1 to 3 as a single isomer. Then, the eluent was removed from each selected fraction with a rotary evaporator, and each of the three kinds of isomers was isolated.

The properties at ordinary temperatures were observed for the isomers A to C isolated as described above. As a result, it was found that the isomers A and C were light yellow solids, and the isomer B was a light yellow liquid. In addition, it was found that the isomers A and C had a melting point of 110° C. and 71° C., respectively, and although the correct melting point of the isomer B was not able to be determined, it was found that the isomer B had a melting point of at least 20° C. or less.

Determination of the Isomer B

By the above purification, the isomer B was isolated as the isomer having two peaks in which the area of the peak in the vicinity of δ 5.40 ppm in the $^1$H-NMR spectrum is equal to that in the vicinity of δ 5.38 ppm. This has revealed that these two peaks are derived from single isomer as assumed in the above. Further, the corresponding isomer has been possible to be specified as the isomer 2 because the corresponding isomer probably contains two kinds of protons which are non-equivalent to each other in the same number in the molecule since the areas of these two peaks are equal to each other. The reason is that the isomer 2 has two kinds of non-equivalent protons in the same number (one) as shown in formula 4. As described above, it has turned out that the isomer B corresponds to the isomer 2.

X-Ray Crystal Structure Analysis (Determination of the Isomer A)

Next, X-ray crystal structure analysis was performed with Rigaku Micro Max-007 (manufactured by Rigaku Corporation) in order to specify the structure of the isomer A. Kα rays of molybdenum monochromatized with graphite (wavelength 0.7107 Å) was used for the radiation source of X-rays. The crystal of the isomer A was cooled to −130° C. with nitrogen gas for use in the measurement. In the analysis of measurement data, a structural analysis software (teXsan) was used. The results are shown in FIG. 3.

Figure 3:
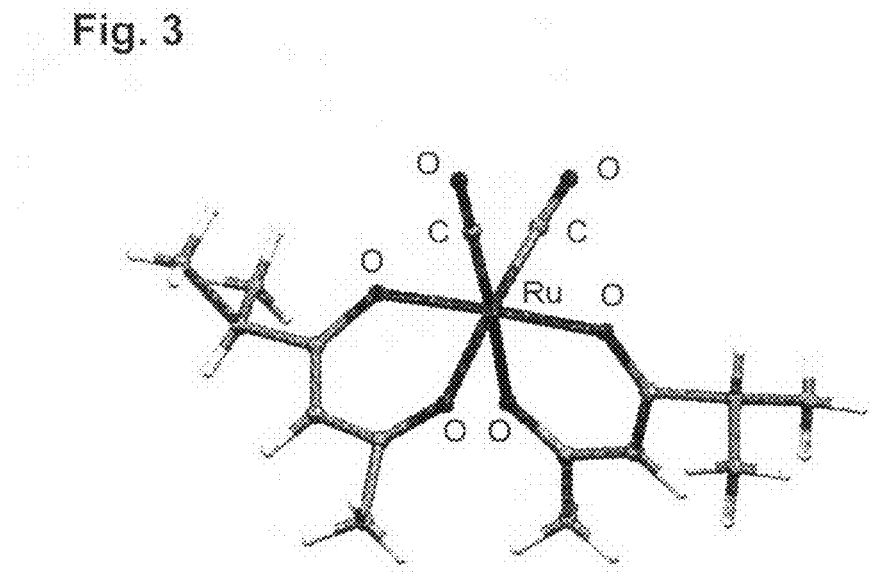
FIG. 3 is a drawing of the results of the X-ray crystal structure analysis of isomer A (the first embodiment).

From FIG. 3, it has been found that the isomer A is the isomer 3 which has a molecular structure in which the isopropyl groups included in the ligands (5-methyl-2,4-hexanedione) are separated from each other (a trans-like structure with respect to the isopropyl groups). Consequently, the X-ray crystal structure analysis has determined that the isomer A is the isomer 3.

Since it has turned out that the isomer A is the isomer 3 and the isomer B is the isomer 2 as described above, it was found that the remaining isomer C was the isomer 1. Next, the proportion (content) of the isomers 1 to 3 in the organoruthenium compound obtained by the synthetic method was measured based on the above relationship. In addition, the relationship between the isomer content and the isomer mixture ratio calculated from the peak area ratio of the $^1$H-NMR spectrum was studied.

Measurement of Isomer Content ($^1$H-NMR Peak Area)

Each content of the isomers 1 to 3 was determined by measuring the peak areas of the $^1$H-NMR spectrum of the compound (including all of the isomers 1 to 3) obtained by the synthetic method. As a result, the peak area ratio in the $^1$H-NMR spectrum was isomer 1:isomer 2:isomer 3=0.29: 0.54:0.17. The peak area ratio can be considered as the isomer content because each isomer has the same molecular weight, and the number of hydrogen atoms of the methine site is also the same as described above. Consequently, the result of the measurement of the peak area ratio has revealed that the content of the isomer 1, the isomer 2, and the isomer 3 is 29%, 54%, and 17%, respectively.

Next, each isomer isolated with column chromatography was mixed so that the resulting mixture might have a specific content, and it was observed how the properties of the organoruthenium compound would change according to the difference in isomer content.

Figure 4:
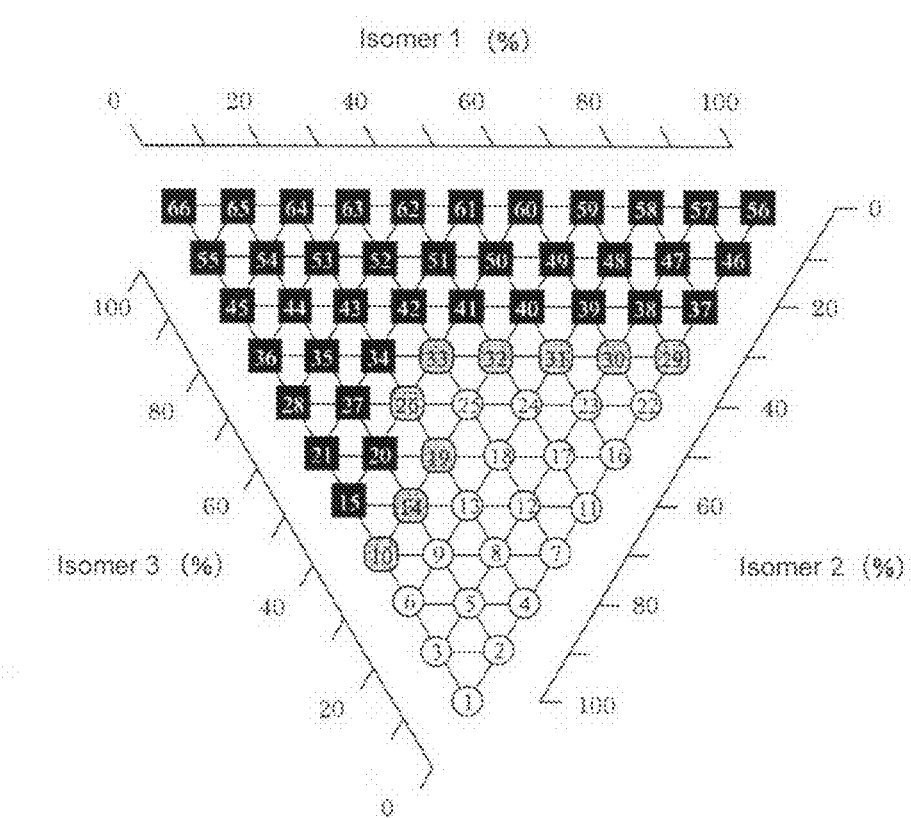
FIG. 4 is a triangular diagram showing the properties of the compounds obtained by mixing the isomers 1 to 3 (the first embodiment).

Observation of the Change of Compound Properties According to the Difference in Isomer Content The mass ratio of the isomers 1 to 3 isolated was adjusted, and the isomers 1 to 3 were mixed at 20° C. so that the resulting mixture might have the isomer content as shown in Table 1 to be described below, thus producing the organoruthenium compounds (No. 1 to 66). The properties (state such as solid or liquid) of the mixed organoruthenium compounds are shown in Table 1. FIG. 4 is a triangular diagram of the results of Table 1 prepared by using the content of the isomers 1, 2, and 3 as an axis. Note that the symbols (○, □, ■) in FIG. 4 represent the properties of the compounds (○ represents liquid; □ represents a mixture of solid and liquid; and ■ represents solid), and the numbers in the symbols correspond to the numbers of the compounds in Table 1.

TABLE 1

| | Content (%) | | | Properties of |
|---|---|---|---|---|
| | Isomer 1 | Isomer 2 | Isomer 3 | compounds |
| 1 | 0 | 100 | 0 | Liquid |
| 2 | 10 | 90 | 0 | Liquid |
| 3 | 0 | 90 | 10 | Liquid |
| 4 | 20 | 80 | 0 | Liquid |
| 5 | 10 | 80 | 10 | Liquid |
| 6 | 0 | 80 | 20 | Liquid |
| 7 | 30 | 70 | 0 | Liquid |
| 8 | 20 | 70 | 10 | Liquid |
| 9 | 10 | 70 | 20 | Liquid |
| 10 | 0 | 70 | 30 | Solid-Liquid |
| 11 | 40 | 60 | 0 | Liquid |
| 12 | 30 | 60 | 10 | Liquid |
| 13 | 20 | 60 | 20 | Liquid |
| 14 | 10 | 60 | 30 | Solid-Liquid |
| 15 | 0 | 60 | 40 | Liquid |
| 16 | 50 | 50 | 0 | Liquid |
| 17 | 40 | 50 | 10 | Liquid |
| 18 | 30 | 50 | 20 | Liquid |
| 19 | 20 | 50 | 30 | Solid-Liquid |
| 20 | 10 | 50 | 40 | Solid |
| 21 | 0 | 50 | 50 | Solid |
| 22 | 60 | 40 | 0 | Liquid |
| 23 | 50 | 40 | 10 | Liquid |
| 24 | 40 | 40 | 20 | Liquid |
| 25 | 30 | 40 | 30 | Liquid |
| 26 | 20 | 40 | 40 | Solid-Liquid |
| 27 | 10 | 40 | 50 | Solid |
| 28 | 0 | 40 | 60 | Solid |
| 29 | 70 | 30 | 0 | Solid-Liquid |
| 30 | 60 | 30 | 10 | Solid-Liquid |
| 31 | 50 | 30 | 20 | Solid-Liquid |
| 32 | 40 | 30 | 30 | Solid-Liquid |
| 33 | 30 | 30 | 40 | Solid-Liquid |
| 34 | 20 | 30 | 50 | Solid |
| 35 | 10 | 30 | 60 | Solid |
| 36 | 0 | 30 | 70 | Solid |
| 37 | 80 | 20 | 0 | Solid |
| 38 | 70 | 20 | 10 | Solid |
| 39 | 60 | 20 | 20 | Solid |
| 40 | 50 | 20 | 30 | Solid |
| 41 | 40 | 20 | 40 | Solid |
| 42 | 30 | 20 | 50 | Solid |
| 43 | 20 | 20 | 60 | Solid |
| 44 | 10 | 20 | 70 | Solid |
| 45 | 0 | 20 | 80 | Solid |
| 46 | 90 | 10 | 0 | Solid |
| 47 | 80 | 10 | 10 | Solid |
| 48 | 70 | 10 | 20 | Solid |
| 49 | 60 | 10 | 30 | Solid |
| 50 | 50 | 10 | 40 | Solid |
| 51 | 40 | 10 | 50 | Solid |
| 52 | 30 | 10 | 60 | Solid |
| 53 | 20 | 10 | 70 | Solid |
| 54 | 10 | 10 | 80 | Solid |
| 55 | 0 | 10 | 90 | Solid |
| 56 | 100 | 0 | 0 | Solid |
| 57 | 90 | 0 | 10 | Solid |
| 58 | 80 | 0 | 20 | Solid |
| 59 | 70 | 0 | 30 | Solid |
| 60 | 60 | 0 | 40 | Solid |
| 61 | 50 | 0 | 50 | Solid |
| 62 | 40 | 0 | 60 | Solid |
| 63 | 30 | 0 | 70 | Solid |
| 64 | 20 | 0 | 80 | Solid |
| 65 | 10 | 0 | 90 | Solid |
| 66 | 0 | 0 | 100 | Solid |

As described above, when the content of the isomer 2 is 30% by mass or more and the content of the isomer 3 is 30% by mass or less, the compounds prepared by mixing each isomer tended to be in a liquid state. Further, when the content of the isomer 2 is 40% by mass or more and the content of the isomer 3 is 20% by mass or less, the resulting compounds were stably in a liquid state without containing solid.

Next, the organoruthenium compounds obtained in the above first embodiment were subjected to evaluation of physical properties and film formation test of ruthenium thin films to verify whether these compounds would be suitable for thin film production.

Evaluation of Physical Properties

Figure 5:
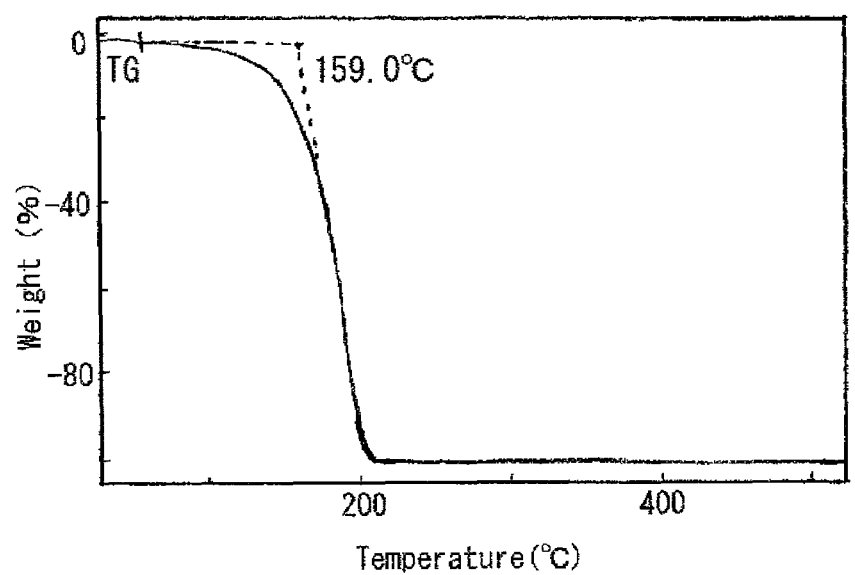
FIG. 5 is a drawing of the results of thermogravimetric analysis (TG) of the organoruthenium compound of the first embodiment.

The organoruthenium compounds obtained by the synthetic method were subjected to measurement of vapor pressure and thermogravimetric analysis (TG). The measurement of vapor pressure was performed using a Pirani gauge (APG-202N32, available from Okano Works Ltd.). Further, the thermogravimetric analysis was performed with Thermo plus TG8120 manufactured by Rigaku Corporation under the conditions of a sample weight of 10 mg, a heating rate of 5° C./min, and under a nitrogen air flow of 200 mL/min. The results of the thermogravimetric analysis are shown in FIG. 5.

As a result of the above measurements, it was found that the organoruthenium compound of the present embodiment had a relatively high vapor pressure, specifically, a vapor pressure at 130° C. of 260 Pa. Further, from the results of the measurement of thermogravimetric analysis shown in FIG. 5, the evaporating temperature calculated by an extrapolation method was 159° C., and it has been verified that it evaporates at a relatively low temperature.

Film Formation Test

Next, the ruthenium thin film was prepared by a CVD process using the organoruthenium compounds obtained by the synthetic method. The film formation conditions were as shown in Table 2. Note that the film formation test was performed under the conditions where oxygen was used as a reactant gas (Example 1), and where hydrogen was used as a reactant gas (Example 2). Further, No. 5 (Example 3) and No. 10 (Example 4) in Table 1, in which the compounds were prepared by isolating each isomer by purification followed by mixing each isomer, were also subjected to film formation (hydrogen was used as a reactant gas). In addition, a film formation test was also performed using the conventional organoruthenium compound in which norbornadiene is coordinated instead of two carbonyl groups in the compounds of formula 2, as shown in formula 5 (Comparative Example 1, hydrogen was used as a reactant gas). Argon was used as a carrier gas during film formation. The results of the film formation are shown in Table 3. Note that the lower the specific resistance shown in the results of Table 3, the more suitable is the ruthenium thin film for semiconductor applications or the like.

[Formula 5]

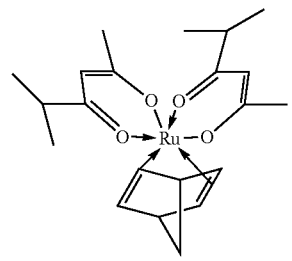

TABLE 2

| | | Film formation conditions | | | | |
|---|---|---|---|---|---|---|
| | Raw material | Reactant gas | Flow rate of carrier gas (sccm) | Flow rate of reactant gas (sccm) | Film formation temperature (° C.) | Film formation pressure (torr) |
| Example 1 | a | Oxygen | 200 | 50 | 300 | 5 |
| Example 2 | a | Hydrogen | 50 | 500 | 350 | 30 |
| Example 3 | b | Hydrogen | 50 | 500 | 350 | 30 |
| Example 4 | c | Hydrogen | 50 | 500 | 350 | 30 |
| Comparative Example 1 | d | Hydrogen | 200 | 500 | 500 | 5 | a: The organoruthenium compound obtained by the synthesis method
b: The compound in which isolated isomers are mixed (No. 5 in Table 1)
c: The compound in which isolated isomers are mixed (No. 10 in Table 1)
d: The conventional organoruthenium compound in which norbornadiene is coordinated (formula 5)

TABLE 3

| | Reactant gas | Film formation temperature | Film formation time | Film thickness | Specific resistance |
|---|---|---|---|---|---|
| Example 1 | Oxygen | 300° C. | 10 min | 35 nm | 33 μΩ cm |
| Example 2 | Hydrogen | 350° C. | 60 min | 30 nm | 23 μΩ cm |
| Example 3 | Hydrogen | 350° C. | 60 min | 30 nm | 25 μΩ cm |
| Example 4 | Hydrogen | 350° C. | 60 min | 15 nm | 50 μΩ cm |
| Comparative Example 1 | Hydrogen | 500° C. | 60 min | 80 nm | 1500 μΩ cm |

As shown in Examples 1 and 2 of Table 3, it was possible to form a ruthenium thin film having a low specific resistance from the organoruthenium compound obtained by the synthetic method, at a relatively low temperature, not only when oxygen (Example 1) was used as a reactant gas, but also when hydrogen (Example 2) was used. Further, as shown in the results of Examples 3 and 4, it was possible to form a ruthenium thin film having a low specific resistance also from the compounds in which isolated isomers are mixed, at a relatively low temperature, when hydrogen was used as a reactant gas. The thin films in Examples 1 and 2 were measured for the surface roughness with a scanning electron microscope (FE-SEM) which was used for measuring the thickness of the films formed, and it was possible to verify that the films are uniform films having a surface roughness of 2 to 3 nm.

On the other hand, it was possible to form a film, though not quite satisfactorily, from the organoruthenium compound of formula 5 (Comparative Example 1) even when hydrogen was used as a reactant gas by increasing the film formation temperature to 500° C., but the formed ruthenium thin film had a relatively high specific resistance.

Second to Fifth Embodiments

The organoruthenium compound was produced in the same manner as in the synthesis of the first embodiment except that the temperature and time to react dodecacarbonyl triruthenium as a raw material were changed (second to fourth embodiments), or the reaction temperature and a solvent were changed (fifth embodiment). The produced compounds were subjected to measurement of isomer content and $^1$H-NMR measurement in the same manner as in the first embodiment.

Second Embodiment: The organoruthenium compound was produced by maintaining the solution temperature during reaction at 140° C. The produced compound was a yellow liquid at ordinary temperatures (yield 70%).

Third Embodiment: The organoruthenium compound was produced by setting the reaction time to 67 hours. The produced compound was a yellow liquid at ordinary temperatures (yield 59%).

Fourth Embodiment: The organoruthenium compound was produced by maintaining the solution temperature during reaction at 80° C. The produced compound was a yellow liquid at ordinary temperatures (yield 14%).

Fifth Embodiment: The organoruthenium compound was produced by using dry hexane as an organic solvent. A stainless steel high-pressure reaction vessel (M50-C: manufactured by OM Lab-Tech Co., Ltd.) was used as a reaction vessel to allow 170 mg (0.266 mmol) of dodecacarbonyl triruthenium, 17 ml of dry hexane (manufactured by Sigma-Aldrich Japan K.K.), and 215 mg (1.68 mmol) of 5-methyl-2,4-hexanedione to react at 160° C. for 24 hours. The pressure at the start of reaction was about 9 atm ($9.11\times10^5$ Pa). Further, the product was distilled at 130° C. and 110 Pa. The produced compound was a yellow liquid at ordinary temperatures (yield 53%).

$^1$H-NMR Spectrum Measurement (Isomer Content)

Figure 6A:
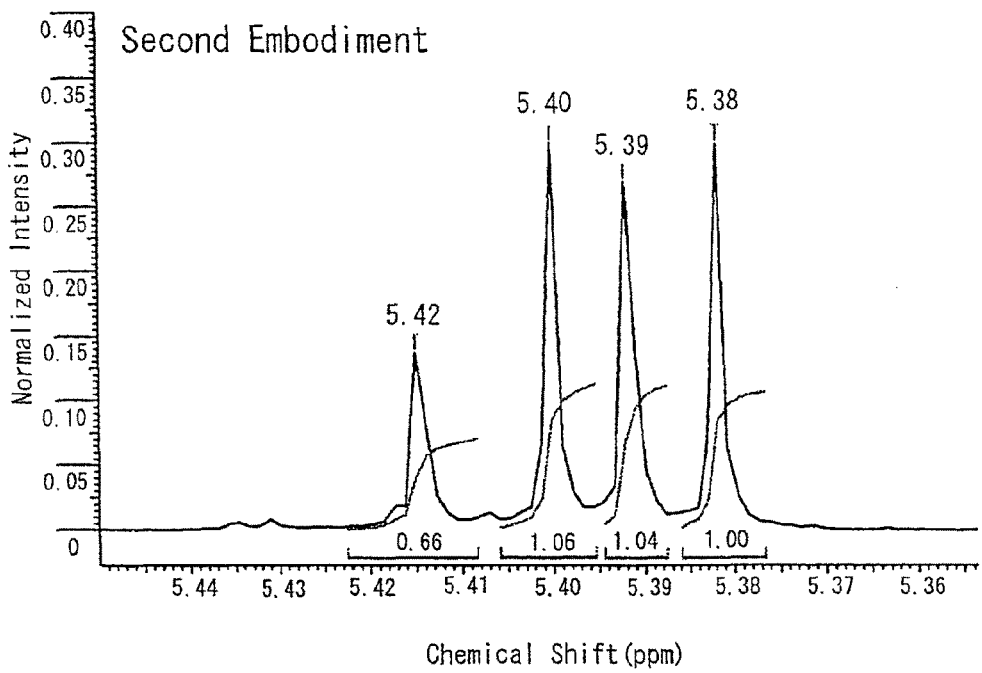
FIGS. 6(a), 6(b), 6(c) show enlarged views of the $^1$H-NMR spectra of the organoruthenium compounds of a second to a fourth embodiment.
Figure 6B:
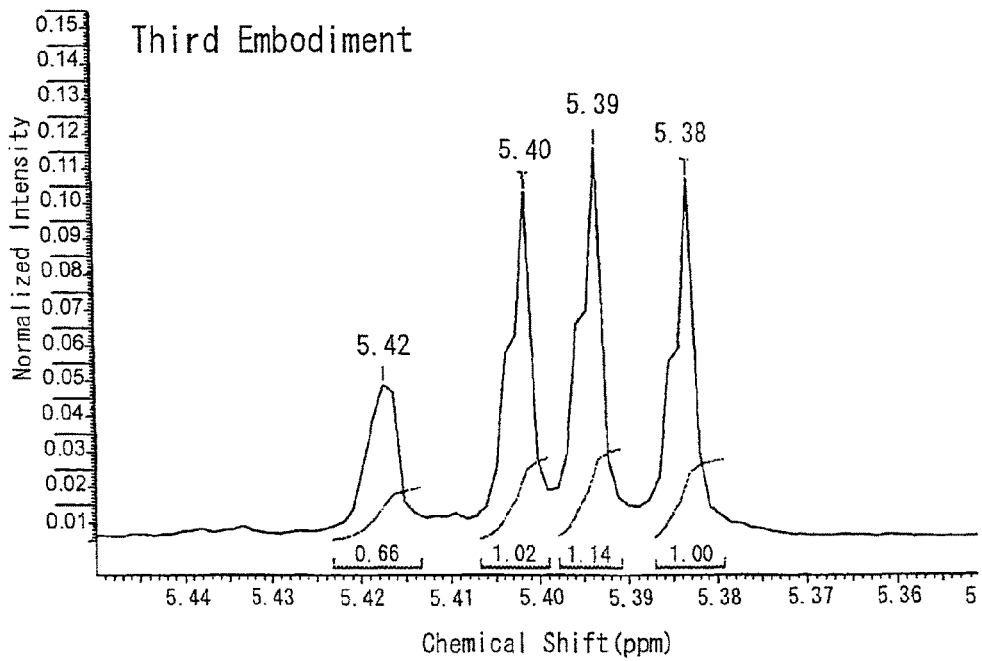
Figure 6C:
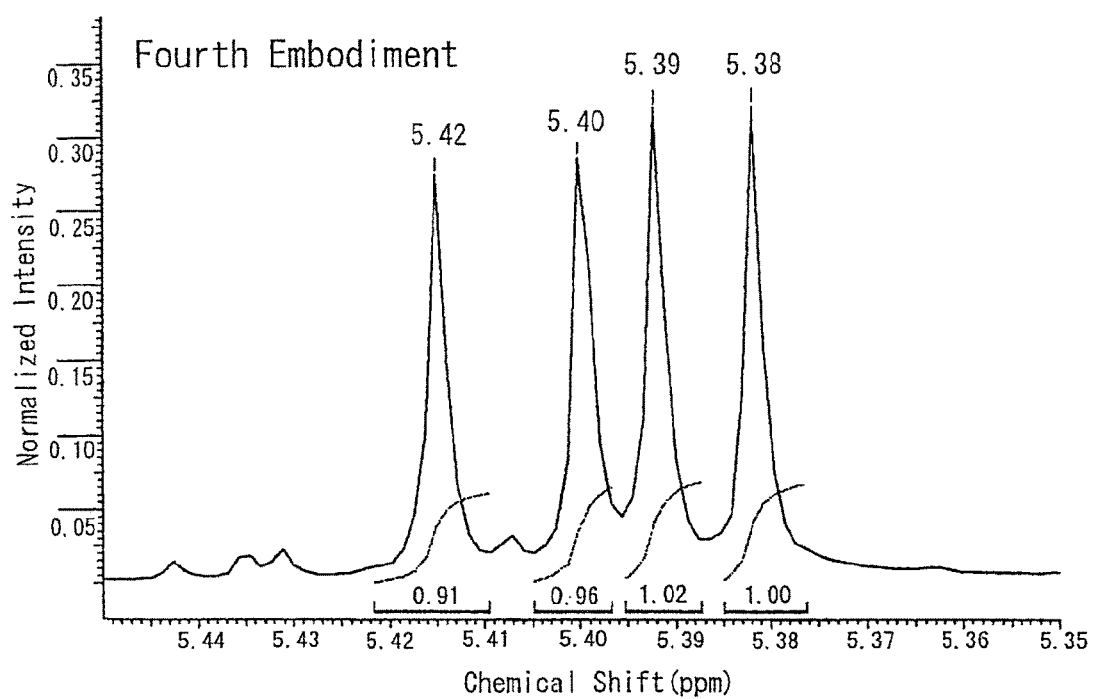

As a result of the $^1$H-NMR measurement for the second to the fifth embodiments, it was found that all the compounds had four peaks in the range of δ 5.38 to 5.42 ppm, which shows that all the compounds include all the isomers 1 to 3. Note that the results of the $^1$H-NMR measurement for the second to the fourth embodiments are shown in FIGS. 6(a), 6(b) and 6(c). Next, the area of each peak and the isomer content (isomer 1:isomer 2:isomer 3) calculated from the peak area, for the four observed peaks, are shown in Table 4.

compound obtained by the synthetic method in the first embodiment (Example 2) were shown together for comparison.

TABLE 5

| | Reactant gas | Film formation temperature | Film formation time | Film thickness | Specific resistance |
|---|---|---|---|---|---|
| First Embodiment* | Hydrogen | 350° C. | 60 min | 30 nm | 23 μΩ cm |
| Second Embodiment | | 350° C. | 60 min | 30 nm | 30 μΩ cm |
| Third Embodiment | | 350° C. | 60 min | 30 nm | 30 μΩ cm |
| Fourth Embodiment | | 350° C. | 60 min | 28 nm | 40 μΩ cm |
| Fifth Embodiment | | 350° C. | 60 min | 29 nm | 35 μΩ cm |

*The first embodiment shows the results of Example 2 (the compound obtained by the synthetic method).

As shown in Table 5, it was possible to form ruthenium thin films each having a low specific resistance and a large film thickness, from the compounds of the first to the third embodiments which were obtained by reacting under the conditions where the solvent was decane, the reaction temperature was in the range of 140 to 160° C., and the reaction time was in the range of 10 to 100 hours, even when hydrogen was used as a reactant gas. On the other hand, in the fourth embodiment in which the solution temperature during the reaction was low (80° C.) and the fifth embodiment in which the pressure during the reaction was high (9 atm ($9.11\times10^5$ Pa), hexane solvent), the specific resistance of the ruthenium thin films tended to be higher.

INDUSTRIAL APPLICABILITY

Since the organoruthenium compound according to the present invention is liquid at ordinary temperatures, it is possible to produce a thin film using a vaporizer which is applied to conventional organoruthenium compounds as it is. In addition, it is possible to stably feed the vaporized reactant gas because the compound itself is liquid, and it is a preferred compound also from the point of view of the maintenance of a deposition apparatus because precipitation of a solid component outside a reactor does not take place.

The invention claimed is:

1. An organoruthenium compound for chemical deposition which has three isomers and is represented by the following formula:

TABLE 4

| | Production method | | | Peak area at each chemical shift value | | | | Isomer content % |
|---|---|---|---|---|---|---|---|---|
| | Solvent | Temperature | Time | 5.42 ppm (A) | 5.40 ppm (B) | 5.39 ppm (C) | 5.38 ppm (B) | (isomer 1:isomer 2:isomer 3) |
| First Embodiment | Decane | 145° C. | 36 hr | 0.61 | 0.96 | 1.05 | 1.00 | 29:54:17 |
| Second Embodiment | Decane | 140° C. | 36 hr | 0.66 | 1.06 | 1.04 | 1.00 | 28:55:18 |
| Third Embodiment | Decane | 140° C. | 67 hr | 0.66 | 1.02 | 1.14 | 1.00 | 30:53:17 |
| Fourth Embodiment | Decane | 80° C. | 36 hr | 0.91 | 0.96 | 1.02 | 1.00 | 26:50:23 |
| Fifth Embodiment | Hexane | 160° C. | 24 hr | 0.73 | 0.98 | 1.03 | 1.00 | 24:49:27 |

Film Formation Test

The compounds of the second to the fifth embodiments were used to prepare ruthenium thin films by a CVD process. The film formation was performed under the same conditions as in the first embodiment (carrier gas: argon, flow rate 50 sccm/reactant gas: hydrogen, flow rate 500 sccm/film formation: temperature 350° C., pressure 30 torr ($4.00\times10^3$ Pa)). The results of the film formation are shown in Table 5. In Table 5, the results of the deposition of the organoruthenium

[Formula 1]

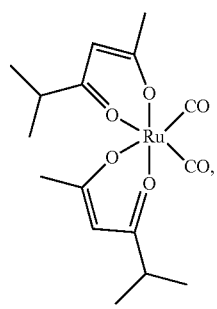

the three isomers being isomer 1, isomer 2, and isomer 3 represented by the following formulas:

[Formula 2]

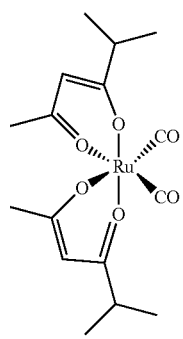

1

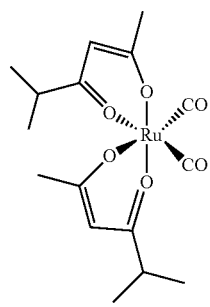

2

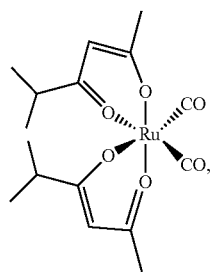

3 wherein the content of the isomer 2 is 30% by mass or more, the content of the isomer 3 is 30% by mass or less, and the balance is the isomer 1.

2. The organoruthenium compound according to claim 1, wherein the content of the isomer 2 is 40% by mass or more, the content of the isomer 3 is 20% by mass or less, and the balance is the isomer 1.

3. A chemical deposition process of a ruthenium thin film or a ruthenium compound thin film comprising vaporizing an organoruthenium compound as a raw material compound to form a reactant gas and heating the reactant gas while introducing the reactant gas into a substrate surface, wherein an organoruthenium compound according to claim 1 is the organoruthenium compound.

4. A chemical deposition process of a ruthenium thin film or a ruthenium compound thin film comprising vaporizing an organoruthenium compound as a raw material compound to form a reactant gas and heating the reactant gas while introducing the reactant gas into a substrate surface, wherein an organoruthenium compound according to claim 2 is the organoruthenium compound.

* * * * *